United States Patent
Wang

(10) Patent No.: US 6,280,454 B1
(45) Date of Patent: Aug. 28, 2001

(54) HEAD ACUPUNCTURE INSTRUMENT

(76) Inventor: Wei-Cheng Wang, 4th Fl., No. 43, Tzu Chiang Hsin Tsun, Panchiao City, Taipei Hsien (TW)

(*) Notice: Subject to any disclaimer, the term of this patent is extended or adjusted under 35 U.S.C. 154(b) by 0 days.

(21) Appl. No.: 09/459,208

(22) Filed: Dec. 10, 1999

(51) Int. Cl.⁷ ................................................. A61B 17/34
(52) U.S. Cl. ........................... 606/189; 600/384; 600/383
(58) Field of Search ..................... 606/189, 181–188; D24/40, 41; 600/583, 575, 587, 383, 384–386; 128/734–735

(56) References Cited

U.S. PATENT DOCUMENTS 4,537,198 * 8/1985 Corbett .................................. 128/639
4,632,122 * 12/1986 Johansson et al. ................... 128/644
4,729,132 * 3/1988 Fierro ........................................ 2/414

* cited by examiner

Primary Examiner—Henry J. Recla
Assistant Examiner—Lien Ngo
(74) Attorney, Agent, or Firm—Thorp Reed & Armstrong, LLP

(57) ABSTRACT

A head acupuncture instrument is disclosed. The head acupuncture instrument includes headgear with electrode probes mounted thereon, a wire dispenser, a plurality of wires extending from an electricity supply to the electrode probes via the wire dispenser, and a column with a bottom end secured to the headgear and a top end extensively received in the wire dispenser. The electrode probes offer stimulating current to acupuncture points needed to be stimulated in a patient's head.

1 Claim, 5 Drawing Sheets

HEAD ACUPUNCTURE INSTRUMENT

BACKGROUND OF THE INVENTION

1. Field of the Invention

The present invention is related to a head acupuncture instrument, and more particularly to a head acupuncture instrument with electrode probes aimed at the acupuncture points for providing stimulating current to the acupuncture point in order to improve the acupuncture effect.

2. Description of Related Art

Acupuncture is a conventional Chinese medical treatment, which relates to piercing a patient's skin at an acupuncture point by a needle for stimulating the acupuncture point in order to achieve the remedial effect. A further form of acupuncture does not involve puncturing the skin, but instead stimulates the acupuncture point by movement or electricity.

In the 1940's, a Japanese inventor invented an "electric needle" related to provide electric current to the needle in order to increase the stimulating effect. Furthermore, in 1957, a French inventor, P. Nogier, invented an ear needle.

It is very difficult for a beginner to locate the exact position of a head acupuncture point, and it is unsafe to use a needle to puncture the head of a patient. For the above reasons, the electric probe is a really safe and effective manner of acupuncture. Because it is difficult to mount the electric probe on the scalp, as in the conventional acupuncture, the doctor has to handle the probes for a long time to gain the necessary skill.

Therefore, it is an objective of the invention to provide a head acupuncture instrument to mitigate and/or obviate the aforementioned problems.

SUMMARY OF THE INVENTION

The main object of the present invention is to provide a head acupuncture instrument with electrode probes aimed at the respective acupuncture points to provide stimulating current to the acupuncture points in order to improve the acupuncture effect.

Another object of the present invention is to provide headgear with electrode probes to mount on the scalp of a patient.

Other objects, advantages and novel features of the invention will become more apparent from the following detailed description when taken in conjunction with the accompanying drawings.

DETAILED DESCRIPTION OF THE PREFERRED EMBODIMENT

Figure 1:
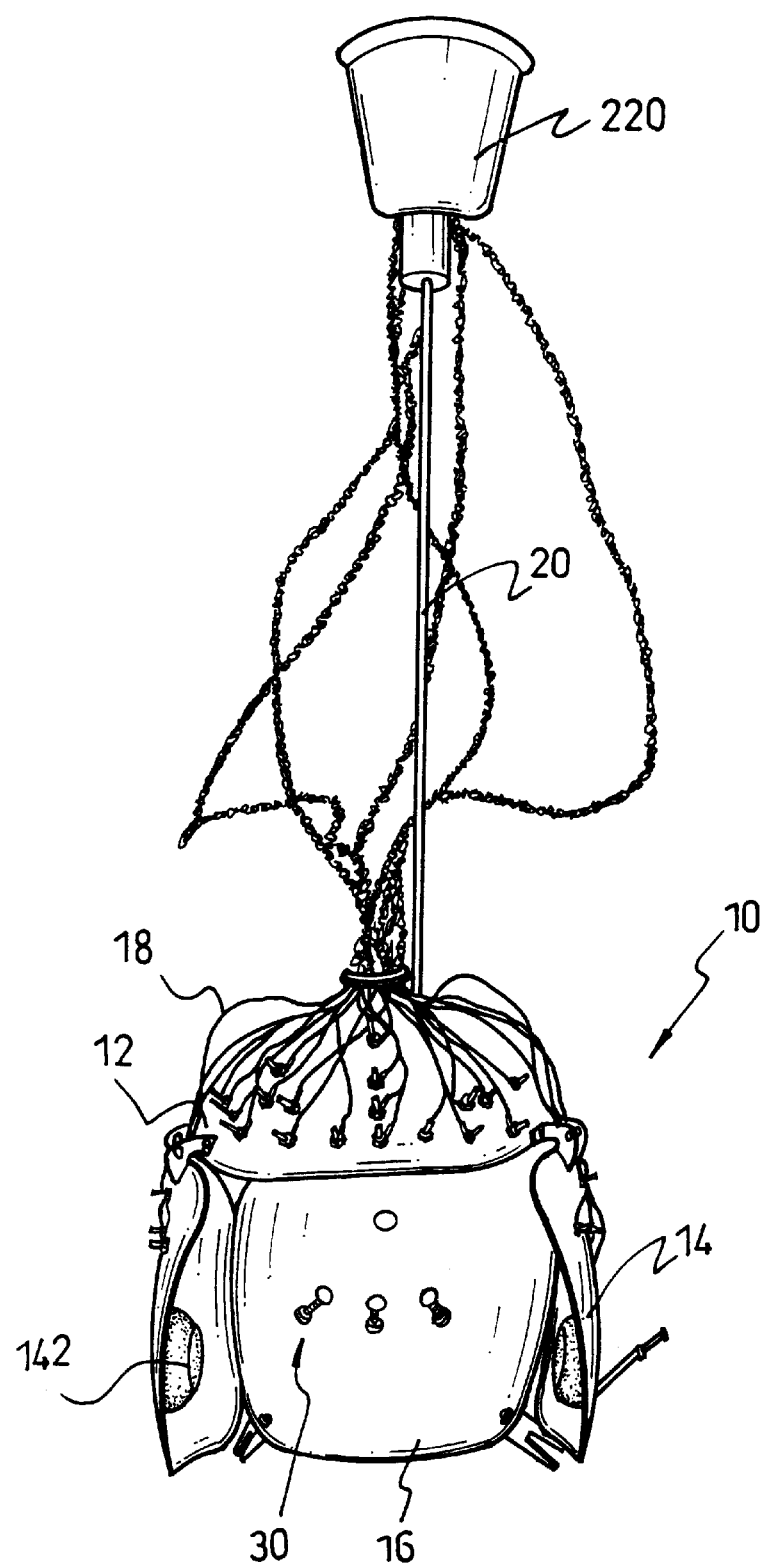
FIG. 1 is a perspective view showing the preferred embodiment of a head acupuncture instrument in accordance with the invention.

Referring to FIG. 1, a head acupuncture instrument of the present invention is disclosed. The head acupuncture instrument mainly comprises a headgear (10), a column (20) with a bottom tip connected to the headgear (10), and a wire dispenser (220) from which the column (20) extends. The wire dispenser (220) is secured to a fixed surface such as a ceiling and allows the column (20) to rise and fall in the same way as the commonly-found rise and fall pendant lamp. The headgear (10) has a plurality of electrode probes (30) which are set in accordance with the various acupuncture points of the head. A plurality of wires (18) extends from the wire dispenser (220) and each wire (18) is connected to a respective one of the electrode probes (30) for providing the stimulating current thereto. The wire dispenser (220) is used to overhang the headgear (10) so that a patient's head will not have to support the weight of the headgear (10).

Figure 2:
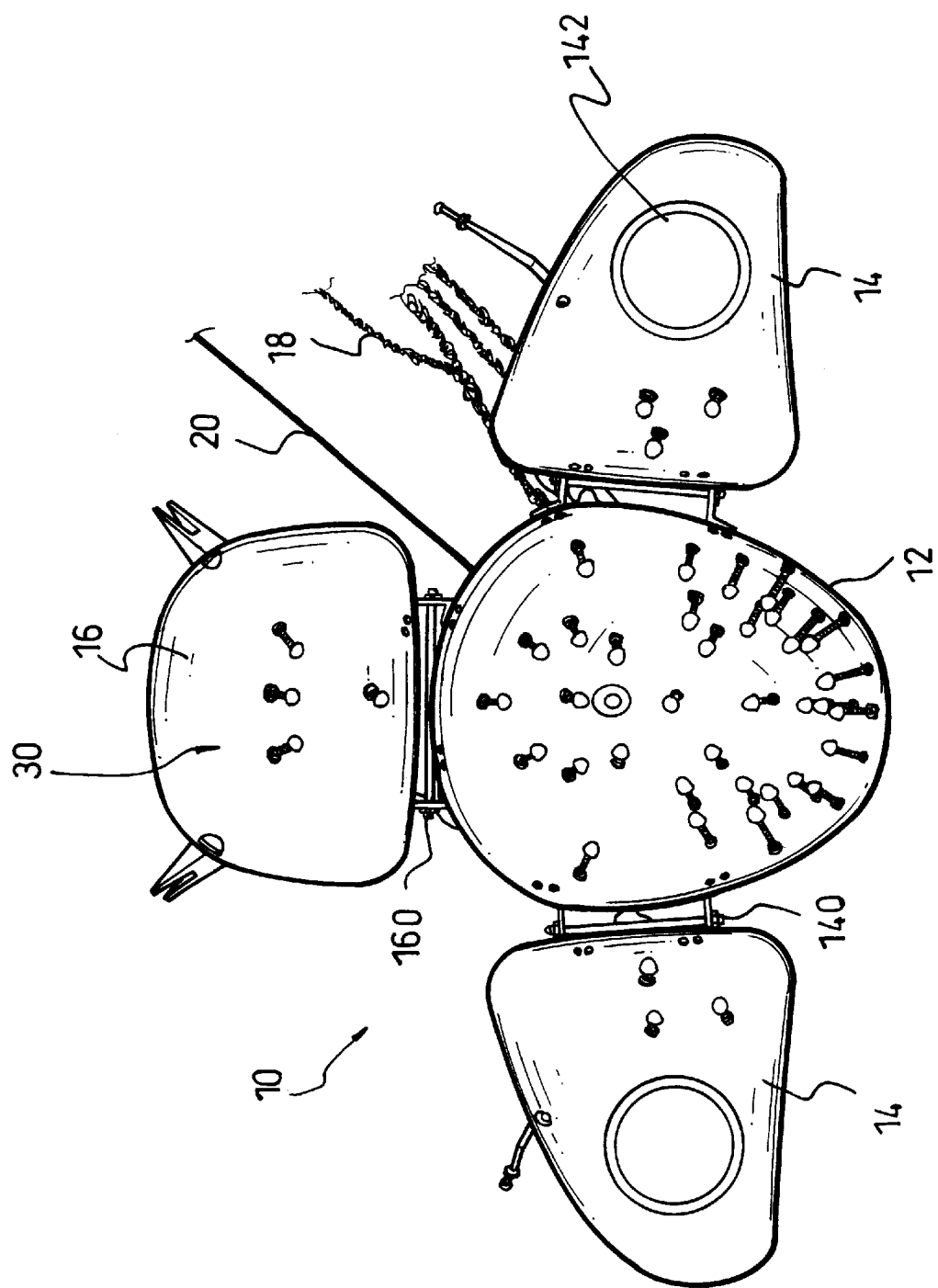
FIG. 2 is a bottom view showing the preferred embodiment of a head acupuncture instrument in accordance with the invention.

Referring to FIG. 2, the headgear (10) consists of a crown (12), two side parts (14) respectively attached to two opposite side edges of the crown (12), and a rear part (16) attached to the crown (12) at a rear edge thereof. The two side parts (14) and the rear part (16) are hinged to the crown (12) with respective hinges (140,160) to permit convenient attachment of the headgear (10) to the head of a patient.

Two earphones (142) are respectively provided on an inside of the side parts (14) of the headgear (10) so as to offer music when the patients are receiving acupuncture treatment. The rhythm of the music is consistent with the frequency of the electric current applied so that the patients will have further stimulation when being treated, which will improve the treatment result to the best degree.

Figure 3:
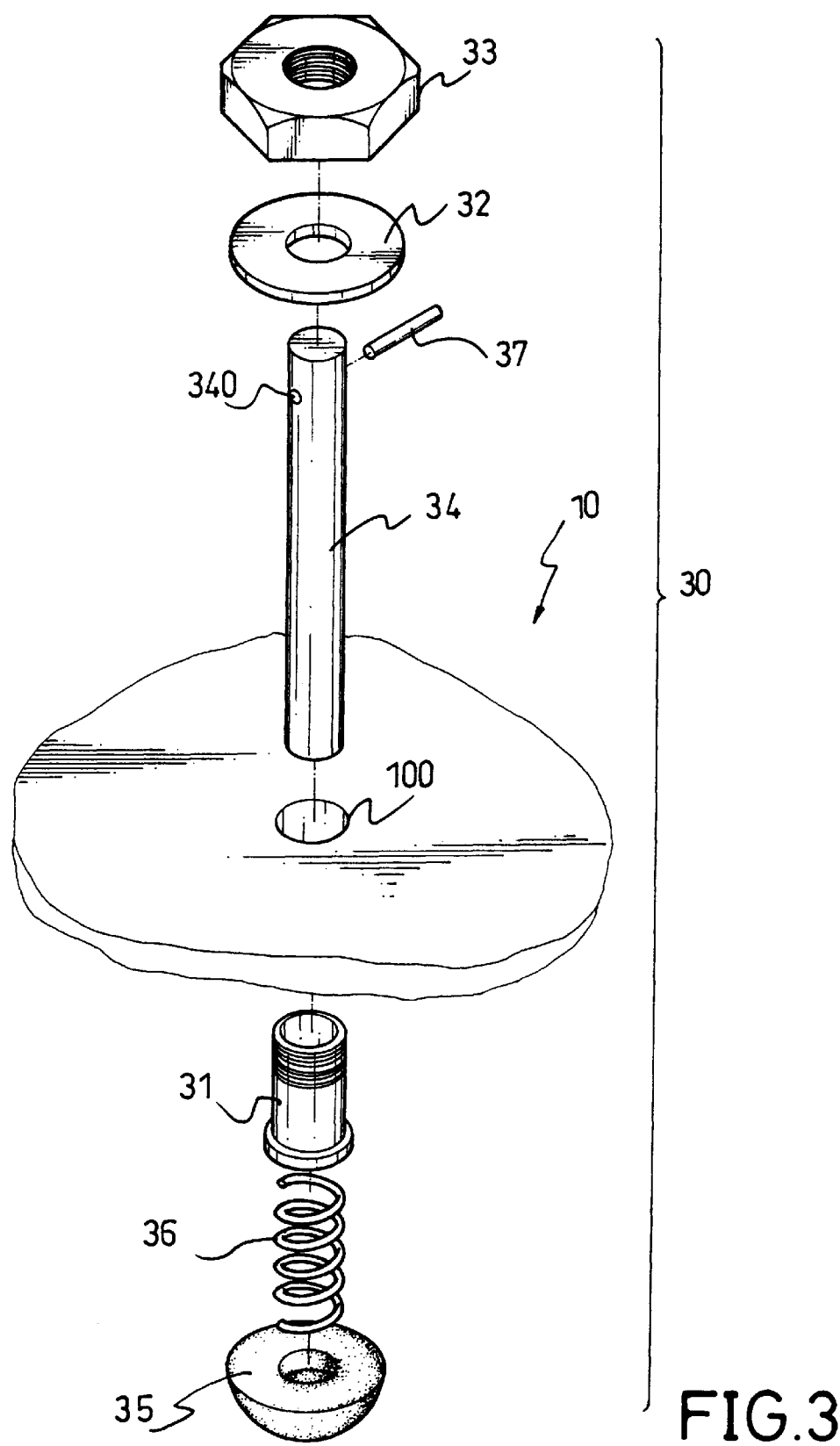
FIG. 3 is an exploded perspective view showing the element of the electrode probe of a head acupuncture instrument in accordance with the invention.

Referring to FIG. 3, each of the electrode probes (30) extends through a respective one of a plurality of through holes (100) defined in the headgear (10). Each through hole (100) is sited at a respective one of the acupuncture points of the patient's head. The electrode probes (30) each comprise a casing pipe (31) with a lipped first end and a threaded second end, a shim (32), a screw nut (33), a mandril (34) with a plain first end and a second end, a pin hole (340) defined transversely through the mandril (34) and near the second end thereof, an electrode cap (35), a spring (36) and a pin (37). The electrode probes (30) are identical and so the assembly steps thereof refer to a singular electrode probe (30).

First, the pipe casing (31) is fitted to the body (10) by extending it through the through hole (100), such that the lipped end thereof abuts an undersurface of the body (10).

Second, the shim (32) is fitted to a portion of the pipe casing (31) protruding from an upper face of the body (10), and after which the screw nut (33) is threadedly engaged with the threaded second end of the pipe casing (31) to secure the pipe casing (31) to the body (10).

Third, the mandril (34) is extended through the casing pipe (31), with the pin hole (340) uppermost and a lowermost portion thereof protruding from the lipped end of the casing pipe (31). The spring (36) is fitted over the lowermost portion of the mandril (34) and retained in position by the cap (35) being securely engaged with the lowermost tip of the mandril (34).

Fourth, the pin (37) is securely extended through the pin hole (340). Thus, the electrode probe (30) is resiliently and slidably retained in the headgear (10).

The spring (36) has a length slightly greater than a length of the mandril (34) such that it is always in compression between the cap (35) and the undersurface of the headgear (10). The second end of the mandril (34) is electrically connected with a respective one of the wires (18).

Figure 4:
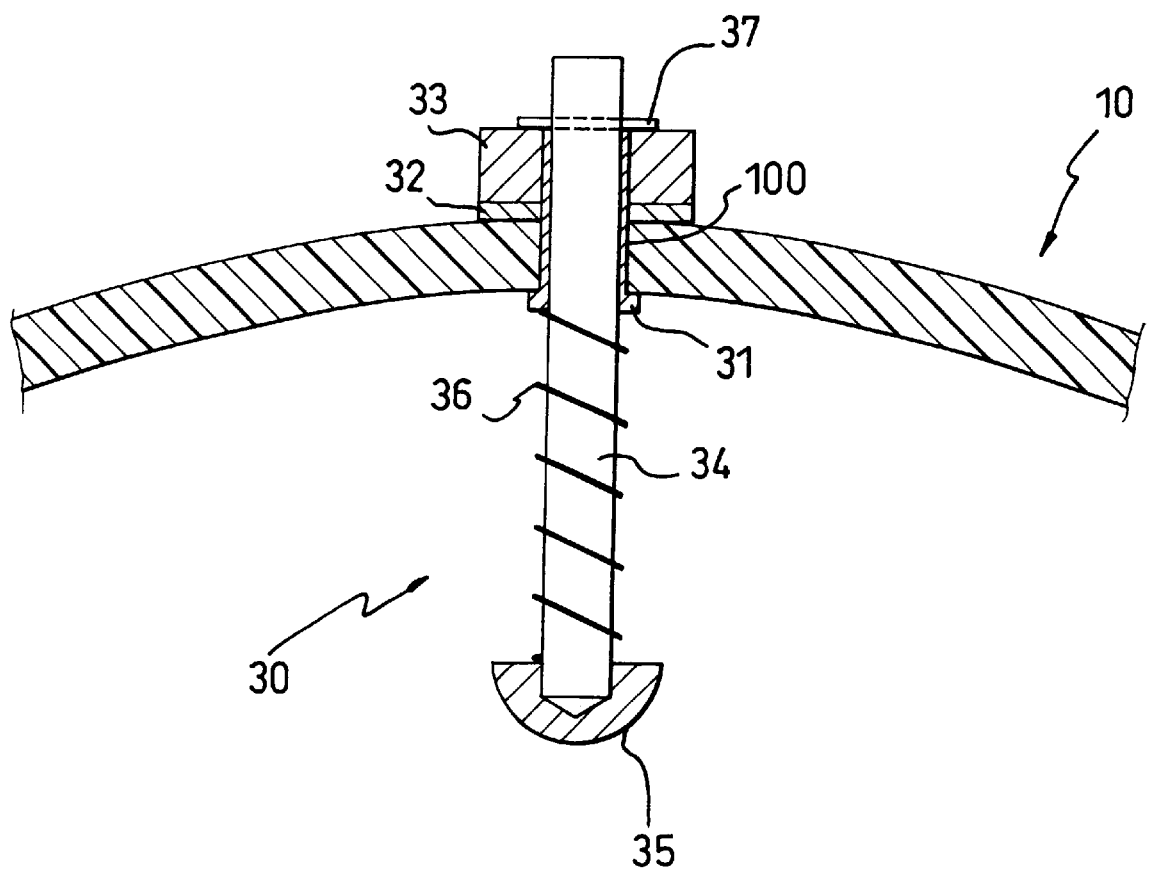
FIG. 4 is a cross sectional view of an electrode probe in accordance with the invention in assembly.
Figure 5:
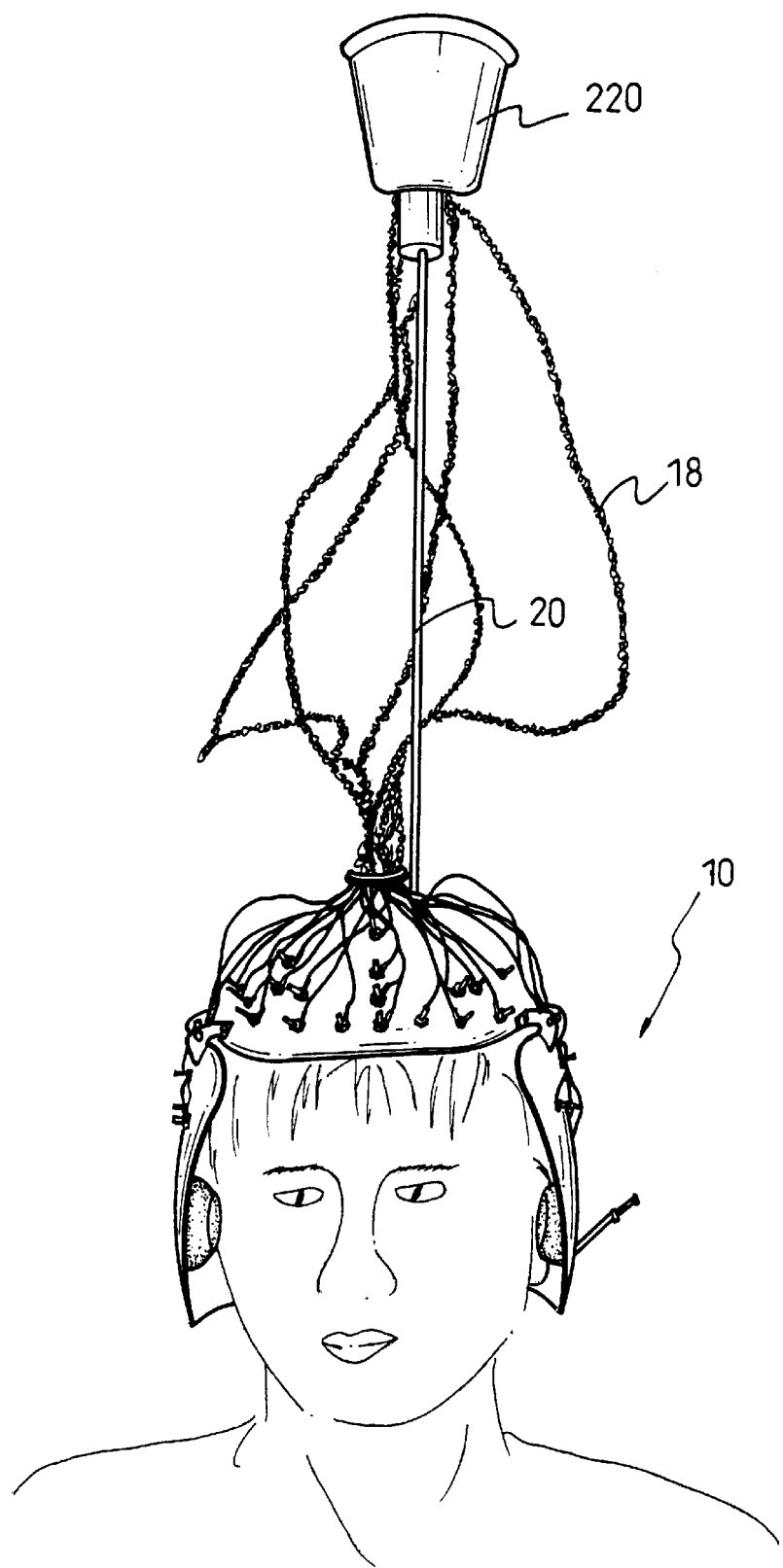
FIG. 5 is a perspective view showing the preferred embodiment of a head acupuncture instrument in accordance with the invention in use.

Referring to FIG. 4, the mandril (34) paired with the spring (36) is retractable through the through hole (100).

Referring to Fig .5, when doctor applies the headgear (10) of this invention correctly, each electrode probe (30) will offer the stimulating current to the respective acupuncture point needing to be stimulated. Moreover, the head acupuncture instrument of this invention can cooperate with computer controlled power to provide each electrode probe (30) the electric current with suitable voltage and frequency timely. Commonly, the voltage of the electric current used is 50–110 Volts and the frequency is 0.3–3.4 kHz.

Furthermore, the electrode cap (35) with the electrode probe (30) can be made of magnetic material with 1500–3500 GS, which can offer a changeable effect of the magnetic field. Specifically, the voltage, the frequency, the acupuncture points and the music rhythm for different patients should be selected and controlled by the computer, and the treatment record should be made in order to improve the acupuncture effect. Headgear (10) of different sizes can be prepared in order to fit different patients.

From the above description, it is noted that the invention has the following advantages:

1. it is highly useful:
    Due to the structure of the invention, the head acupuncture instrument can effectively treat the patient by acupuncture.
2. excellent safety:
    Because of the structure of the invention, the head acupuncture instrument can safely treat the patient by acupuncture.

It is to be understood, however, that even though numerous characteristics and advantages of the present invention have been set forth in the foregoing description, together with details of the structure and function of the invention, the disclosure is illustrative only, and changes may be made in detail, especially in matters of shape, size, and arrangement of parts within the principles of the invention to the full extent indicated by the broad general meaning of the terms in which the appended claims are expressed.

What is claimed is:

1. A head acupuncture instrument comprising:

headgear including a crown, two side parts hinged to said crown; and a rear part hinged to said crown; a plurality of electrode probes, each having a casing pipe, and each extending through one of a plurality of through holes defined in said headgear; a mandril extending through said casing pipe with a spring mounted around a lower portion of said mandril and compressed between an electrode cap mounted on a bottom end of said mandril and an undersurface of the headgear; a pin mounted through a pin hole provided in said mandril and above an outer surface of said headgear whereby said mandril is fixed in said casing pipe;

wherein said electrode cap is made of magnetic material with 1500–3500 GS, which offers a changeable effect of a magnetic field and wherein each electrode probe is directed toward a respective acupuncture point of a patient's head;

a wire dispenser;

a plurality of wires extending through said wire dispenser, each of said wires having a first end connected to an electricity supply and a second end connected to a respective one of said electrode probes;

at least one earphone provided on an inside surface of said side parts; and support means with a bottom end secured to the headgear and a top end received in said wire dispenser; whereby electric current is received in each said electrode probe and a patient wearing said head acupuncture instrument can receive head acupuncture treatment and can further simultaneously receive aural therapy such as music.

* * * * *